US007128933B2

(12) United States Patent
Kurk et al.

(10) Patent No.: US 7,128,933 B2
(45) Date of Patent: Oct. 31, 2006

(54) COMPOSITION AND METHOD FOR THE TREATMENT OF PERSONAL ODORS

(76) Inventors: Mitchell Kurk, 310 Broadway, Lawrence, NY (US) 11559; Odilza Vital, Av. Ary Parreiras No'327, Niteról, RJ 24230-320 (BR)

( * ) Notice: Subject to any disclaimer, the term of this patent is extended or adjusted under 35 U.S.C. 154(b) by 294 days.

(21) Appl. No.: 10/439,971

(22) Filed: May 16, 2003

(65) Prior Publication Data
US 2003/0228384 A1    Dec. 11, 2003

Related U.S. Application Data

(63) Continuation-in-part of application No. 09/945,059, filed on Aug. 31, 2001, now abandoned.

(60) Provisional application No. 60/229,864, filed on Sep. 1, 2000.

(51) Int. Cl.
*A01N 65/00* (2006.01)
*A61K 9/48* (2006.01)
*A61K 9/20* (2006.01)
*A61K 36/53* (2006.01)

(52) U.S. Cl. ............... 424/745; 424/451; 424/453; 424/455; 424/725; 424/739; 424/746; 514/962

(58) Field of Classification Search ........... 424/400, 424/439, 440, 441, 451, 49, 725, 746, 739; 514/962
See application file for complete search history.

(56) References Cited

U.S. PATENT DOCUMENTS 2,643,212 A    6/1953  Philippin
3,963,786 A *  6/1976  Karrer et al. ............... 568/637
4,144,199 A *  3/1979  Wille et al. .................. 512/24
4,318,906 A    3/1982  Llopart
4,525,342 A *  6/1985  Weiss et al. ................. 424/49
4,576,742 A *  3/1986  Sprecker et al. ............ 510/105
4,880,639 A * 11/1989  Lauermann et al. .......... 426/2
5,770,217 A *  6/1998  Kutilek et al. .............. 424/442
6,066,649 A *  5/2000  Podzuweit ................... 514/303
6,197,305 B1   3/2001  Friedman et al.
6,221,346 B1*  4/2001  Streels ....................... 424/69
6,555,093 B1*  4/2003  Alvarez Hernandez ...... 424/48

FOREIGN PATENT DOCUMENTS

| CH | 688787 | * | 3/1998 |
| EP | 0 321 180 A | | 6/1989 |
| ES | 2067373 | * | 3/1995 |
| FR | 2631824 | * | 12/1989 |
| FR | 2702654 | * | 9/1994 |
| JP | 10 245343 A | | 9/1998 |

OTHER PUBLICATIONS

Edwards (The Aromatherapy Companion ).*
Database WPI, Section Ch, Week 198950, Derwent Publications Ltd., London, GB; AN 1989-229013—XP002266443 & JP 01 275522 A (Sanwa Kagaku Kenkyusho Co), Nov. 6, 1989 abstract.

* cited by examiner

*Primary Examiner*—Sharmila S. Gollamudi
(74) *Attorney, Agent, or Firm*—Renner, Otto, Boisselle and Sklar, LLP

(57) ABSTRACT

An orally ingestible composition for the treatment of external personal odors can include about 35% w/w to about 50% w/w of the essential oil of lavender, about 1% w/w to about 10% w/w of the essential oil of rosemary, about 1% w/w to about 10% w/w of the essential oil of sage, and sufficient carrier medium to make up to 100% by weight.

14 Claims, No Drawings

COMPOSITION AND METHOD FOR THE TREATMENT OF PERSONAL ODORS

CROSS-REFERENCE TO RELATED APPLICATIONS

This application is a continuation-in-part of application Ser. No. 09/945,059, filed Aug. 31, 2001 now abandoned, which claims the benefit of Provisional Application No. 60/229,864, filed on Sep. 1, 2000. The entire disclosure of application Ser. No. 09/945,059 is incorporated herein by reference.

TECHNICAL FIELD

The present invention relates generally to compositions for reducing odors in humans and, more particularly, to a composition and method suitable for the treatment of personal external odors.

BACKGROUND

The main function of an anti-odor composition is that of preventing or otherwise minimizing body malodor due to bacterial decompositions and to the oxidation of the organic substances that are components of perspiration. Previous methods of reducing and/or eliminating personal odors include perfumes, underarm deodorants and antiperspirants, vaginal douches and suppositories, and deodorant soaps. In addition, chlorophyll pills have been administered orally to reduce both internal and external body odors. Unfortunately, these products are not always effective.

Accordingly, a need exists for a new and improved composition and method for eliminating external personal odors, which overcome the above-referenced problems and others.

SUMMARY OF THE INVENTION

According to one aspect of the invention, the invention is directed to an orally ingestible composition for the treatment of external personal odors. The composition can include about 35% w/w to about 50% w/w of the essential oil of lavender. The composition can further include about 1% w/w to about 10% w/w of the essential oil of rosemary and about 1% w/w to about 10% w/w of the essential oil of sage. The composition can further include a sufficient amount of carrier medium to make up to 100% by weight.

According to another aspect of the invention, the invention is directed a method for reducing external personal odors in a subject. The method can include orally administering at least twice per day to the subject an ingestible composition. The ingestible composition can comprise about 35% w/w to about 50% w/w of the essential oil of lavender, about 1% w/w to about 10% w/w of the essential oil of rosemary, and about 1% w/w to about 10% w/w of the essential oil of sage.

According to another aspect of the invention, the invention is directed to an orally ingestible composition for the treatment of external personal odors. The composition can include about 50% w/w of an olive oil based carrier medium and about 50% w/w of a mixture. The mixture can comprise about 90% w/w of the essential oil of lavender, about 5% w/w of the essential oil of rosemary, and about 5% w/w of the essential oil of sage.

DISCLOSURE OF INVENTION

The present invention provides a suitable composition for the treatment and/or prevention of external personal odors. The composition is an orally ingestible composition comprising essential oils of rosemary, lavender, and sage.

Essential oils are aromatic molecules found in fragrance plants. The aromatic molecules are extracted, creating very concentrated liquids that are tens to hundreds of times stronger than when in the plant. Those skilled in the art will appreciate that such essential oils may be extracted from the plants by a variety of conventional methods, such as steam/water distillation, including turbo and continuous distillation, cold pressing, and carbon dioxide gas extraction.

Rosemary is a plant whose essential oil has been used in aroma therapy applications to stimulate the central nervous system and in body and skin care. its main chemical components include 1,8-Cineole, Beta Pinene, Camphor, Camphene, Borneol, and Bornyl Acetate. Essential oil of rosemary enjoys the following properties, among others: antimicrobial, antiseptic, analgesic, and antidepressant.

Lavender oil is a natural antibiotic, antiseptic, antidepressant, sedative, and detoxifier which promotes healing and prevents scarring. Its main chemical components are Linalyl Acetate, Linalol, Geraniol, Borneol, Isobornyl, and Cineol-1,8.

Sage is a plant whose essential oil has been used to treat sores, bacterial infections, bronchitis, catarrh, rheumatism, arthritis, sprains, fibrosis, and excessive perspiration. Its main chemical components are Linalol, Linalyl Acetate, Germacrene, and Ceranyl Acetate.

In one embodiment, the composition comprises about 50% by weight (w/w) of a mixture of essential oils and about 50% by weight of a carrier medium or base. In one embodiment, the mixture of essential oils includes the essential oils of rosemary, lavender and sage. In an alternative embodiment, the composition can include a mixture of the essential oils of rosemary, lavender and sage along with other essential oils, including, but not limited to, vanilla oil, cinnamon oil, sunflower oil, coconut oil, rosewood oil, pineapple oil, and primrose oil.

In one embodiment, a suitable orally ingestible composition for the treatment of external personal odors includes:

| Component | % by weight (w/w) |
| --- | --- |
| Essential oil of lavender | 35–50 |
| Essential oil of rosemary | 1–10 |
| Essential oil of sage | 1–10 |
| Carrier medium | 35–65 |

However, it is to be appreciated that other ratios of the essential oils of rosemary, lavender, and sage may be employed.

In an alternative embodiment, a suitable orally ingestible composition for the treatment of external personal odors includes:

| Component | % by weight (w/w) |
| --- | --- |
| Essential oil of lavender | 30–40 |
| Essential oil of rosemary | 1–4 |
| Essential oil of sage | 1–4 |
| Vanilla oil | 4–12 |
| Cinnamon oil | 1–4 |
| Carrier medium | 35–65 |

However, it is to be appreciated that other ratios of the essential oils of rosemary, lavender, sage, vanilla and cinnamon may be employed.

The composition can be delivered or otherwise presented in a soft gel or hard capsule (e.g., a two-piece vegetable liquid capsule) by mixing the active ingredients with the carrier medium and enclosing them within a soft gel or hard capsule. In one embodiment, the base or carrier medium includes olive oil. The olive oil can optionally be mixed with other ingredients, including, but not limited to, candelilla wax, lecithin (e.g., non-genetically modified (non-GMO)), hydroxypropylmethylcellulose, water, peanut oil and liquid paraffin.

In an alternative embodiment, the composition is administered in an oral liquid dosage form by suspending the active ingredients or extracts thereof in an aqueous solution in admixture with a dispersing or wetting agent, suspending agent, and one or more preservatives. Suitable dispersing or wetting agents include naturally occurring phosphatides, for example, lecithin, or condensation products of ethylene oxide, fatty acids, and long chain aliphatic acids. Other suitable liquid forms include, for example, elixirs, syrups and potions. Other suitable preparations for oral administration may be employed without departing from the scope of the present invention.

EXAMPLE 1

In one preferred embodiment, a suitable orally ingestible composition for the treatment of external personal odors comprises about 50% w/w of a base of olive oil with candelilla wax, non-GMO lecithin and hydroxypropylmethylcellulose and about 50% w/w of a mixture including about 90% w/w of the essential oil of lavender, about 5% w/w of the essential oil of rosemary, and about 5% w/w of the essential oil of sage.

EXAMPLE 2

Uncoated 500 mg two-piece vegetable liquid capsules were prepared containing about 10 drops per capsule of the composition obtained in EXAMPLE 1. Each capsule included about 10 drops of a blend of Food Grade:

| Component | weight (mg) |
|---|---|
| Essential oil of lavender | 203 mg |
| Essential oil of rosemary | 12 mg |
| Essential oil of sage | 12 mg |
| Olive Oil | 225 mg |

In one embodiment, the 500 mg per capsule dosage of the composition obtained in EXAMPLE 1 can be administered to a subject at least two times per day and, preferably, three times daily, preferably before meals. It is to be appreciated that the dosage may be modified depending on effectiveness in a given patent.

While the present invention has been described with reference to a composition suitable for the treatment of external odors in humans, it is to be appreciated that it finds application in the treatment of internal and external odors in animals as well.

Although, particular embodiments of the invention have been described in detail, it is understood that the invention is not limited correspondingly in scope, but includes all changes, modifications, and equivalents coming within the spirit and terms of the claims appended hereto. In addition, it is to be appreciated that features shown and described with respect to a given embodiment may also be used in conjunction with other embodiments.

What is claimed is:

1. An orally ingestible composition for the treatment of personal odors, said composition comprising:
   about 40% w/w to about 45% w/w of the essential oil of lavender;
   about 2% w/w to about 5% w/w of the essential oil of rosemary;
   about 2% w/w to about 5% w/w of the essential oil of sage; and
   sufficient carrier medium to make up 100% by weight, wherein the carrier medium is selected from the group consisting of peanut oil, liquid paraffin and olive oil; and
   wherein the composition is in an oral solid form.

2. The composition as set forth in claim 1, comprising:
   about 40% w/w of the essential oil of lavender;
   about 5% w/w of the essential oil of rosemary;
   about 5% w/w of the essential oil of sage; and
   about 50% w/w of the carrier medium.

3. An orally ingestible composition for the treatment of personal odors, said composition comprising:
   about 45% w/w of the essential oil of lavender;
   about 2.5% w/w of the essential oil of rosemary;
   about 2.5% of the essential oil of sage; and
   about 50% w/w of a carrier medium, wherein the carrier medium is selected from the group consisting of peanut oil, liquid paraffin, and olive oil.

4. The composition as set forth in claim 3, wherein the carrier medium is olive oil.

5. The composition as set forth in claim 3, wherein the composition is in an oral solid form.

6. The composition as set forth in claim 5, wherein the oral solid form is a soft capsule.

7. The composition as set forth in claim 6, wherein the oral solid form is a two-piece vegetable capsule.

8. The composition as set forth in claim 5, wherein the oral solid forms is a hard capsule.

9. The composition as set forth in claim 1, further comprising:
   about 4% w/w to about 12% w/w of vanilla oil; and
   about 1% w/w to about 4% w/w of cinnamon oil.

10. A method for reducing external personal odors in a subject, said method comprising:
    orally administering at least twice per day to the subject an ingestible composition comprising:
    about 40% w/w to about 45% w/w of the essential oil of lavender;
    about 2% w/w to about 5% w/w of the essential oil of rosemary;
    about 2% w/w to about 5% w/w of the essential oil of sage, and
    sufficient carrier medium to make up 100% by weight, wherein the carrier medium is selected from the group consisting of peanut oil, liquid paraffin and olive oil; and
    wherein the composition is in an oral solid form.

11. The method as set forth in claim 10, wherein the orally administering step includes:
    mixing the essential oils of lavender, rosemary, and sage with olive oil as the carrier medium,
    delivering the mixture of essential oils and olive oil in a two-piece vegetable capsule,
    administering the capsule to the subject orally.

12. The method as set forth in claim 11, wherein the orally administering step includes administering the ingestible composition in the form of a 500 mg capsule to the subject three times per day.

13. An orally ingestible composition for the treatment of external personal odors, said composition comprising:
- about 50% w/w of an olive oil based carrier medium; and
- about 50% w/w of a mixture comprising:
  - about 90% w/w of the essential oil of lavender;
  - about 5% w/w of the essential oil of rosemary; and
  - about 5% w/w of the essential oil of sage.

14. The composition as set forth in claim 13, wherein the carrier medium further comprises:
- non-GMO lecithin, and hydroxypropylmethylcellulose.

* * * * *